United States Patent
Cheng et al.

(10) Patent No.: US 7,655,906 B2
(45) Date of Patent: Feb. 2, 2010

(54) METHOD AND APPARATUS FOR SCANNING AND MEASUREMENT BY ELECTRON BEAM

(75) Inventors: Zhaohui Cheng, Tokyo (JP); Hiroshi Makino, Kokubunji (JP); Hikaru Koyama, Kodaira (JP); Mitsugu Sato, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 152 days.

(21) Appl. No.: 11/503,997

(22) Filed: Aug. 15, 2006

(65) Prior Publication Data

US 2007/0040118 A1 Feb. 22, 2007

(30) Foreign Application Priority Data

Aug. 19, 2005 (JP) ............................. 2005-238105

(51) Int. Cl.
*G21K 7/00* (2006.01)
*G01N 23/00* (2006.01)
*H01J 37/29* (2006.01)

(52) U.S. Cl. ........................ 250/307; 250/306; 250/310; 250/311; 250/399

(58) Field of Classification Search ......... 250/305–307, 250/310, 311, 396 R, 397, 399
See application file for complete search history.

(56) References Cited

U.S. PATENT DOCUMENTS

| | | | | |
|---|---|---|---|---|
| 4,355,232 A | * | 10/1982 | Todokoro et al. | 250/310 |
| 5,369,359 A | * | 11/1994 | Schmitt | 324/158.1 |
| 2002/0109090 A1 | * | 8/2002 | Nakasuji et al. | 250/311 |
| 2003/0127593 A1 | * | 7/2003 | Shinada et al. | 250/310 |
| 2004/0065827 A1 | * | 4/2004 | Kienzle et al. | 250/311 |
| 2004/0211899 A1 | * | 10/2004 | Ezumi et al. | 250/310 |
| 2005/0045821 A1 | * | 3/2005 | Noji et al. | 250/311 |
| 2005/0099189 A1 | * | 5/2005 | Cheng et al. | 324/751 |
| 2005/0161600 A1 | * | 7/2005 | Ezumi et al. | 250/310 |
| 2005/0173644 A1 | * | 8/2005 | Gnauck et al. | 250/370.11 |
| 2005/0279935 A1 | * | 12/2005 | Shur et al. | 250/310 |
| 2006/0006330 A1 | * | 1/2006 | Seyama et al. | 250/310 |
| 2006/0028218 A1 | * | 2/2006 | Cheng et al. | 324/751 |
| 2006/0169900 A1 | * | 8/2006 | Noji et al. | 250/310 |
| 2007/0040118 A1 | * | 2/2007 | Cheng et al. | 250/310 |
| 2007/0228276 A1 | * | 10/2007 | Makino et al. | 250/310 |
| 2008/0017797 A1 | * | 1/2008 | Cheng et al. | 250/310 |

FOREIGN PATENT DOCUMENTS

JP 61-239554 10/1986

OTHER PUBLICATIONS

A. Gopinath, Voltage Contrast, Scanning Electron Microscopy, 1978, vol. I, pp. 375-380.

* cited by examiner

*Primary Examiner*—Bernard E Souw
(74) *Attorney, Agent, or Firm*—Antonelli, Terry, Stout & Kraus, LLP.

(57) ABSTRACT

An inspection and measurement method and apparatus for semiconductor devices and patterns such as photomasks using an electron beam capable of measuring the potential of a sample with higher precision than conventional systems. When an S curve is observed in a semiconductor device to be inspected, fluctuations of the potential of the inspection sample surface are suppressed by optimizing the energy of a primary electron beam used for irradiation. When the surface potential of the semiconductor device is measured, a more precise measurement can be obtained without adverse effects from an insulation film surface. Further, the surface potential can be measured without installing a special apparatus for wafer surface potential measurement such as an energy filter, so the cost of the apparatus can be reduced.

18 Claims, 11 Drawing Sheets

METHOD AND APPARATUS FOR SCANNING AND MEASUREMENT BY ELECTRON BEAM

CLAIM OF PRIORITY

The present application claims priority from Japanese application JP No. 2005-238105 filed on Aug. 19, 2005, the content of which is hereby incorporated by reference into this application.

FIELD OF THE INVENTION

The present invention relates to a method of manufacturing a fine circuit pattern formed on a substrate such as a semiconductor device or liquid crystal, and in particular relates to a method of pattern inspecting and measurement of a semiconductor device and photomask by an electron beam.

BACKGROUND OF THE INVENTION

A semiconductor device is manufactured by repeatedly performing a process which transfers a pattern formed on a photomask to a semiconductor wafer by lithography and etching. In this manufacturing process, the quality of lithography, etching and other steps, and the production of foreign matter, largely affect the yield of the semiconductor device, so in the semiconductor manufacturing field, it is important to have a method for early or prior detection when a fault occurs in the manufacturing process. In the prior art, a pattern inspecting and measurement apparatus employing an optical microscope was conventionally used, but in recent years, semiconductor devices have become more intricate while manufacturing processes have become more complex, so the use of electron microscopes is becoming more widespread.

One such appliance which uses an electron microscope is a circuit pattern inspection apparatus employing the Scanning Electron Microscopy (hereafter, SEM inspection apparatus). Many defects can be detected by this inspection apparatus such as electrical defects, adhesion of foreign matter, pattern shape defects, etc., and since an optical inspection apparatus cannot detect electrical defects, this special function of the SEM inspection apparatus is now attracting attention in the semiconductor manufacturing field. The detection of electrical defects in a semiconductor device by this SEM inspection apparatus is performed by charging a circuit pattern formed in a wafer surface, and using the contrast visualized by the charging. This is referred to as the voltage contrast method, and it is effective in detecting defective electrical properties of the semiconductor device.

Hereafter, the mechanism of forming a voltage contrast will be described using FIG. 2. FIG. 2 is a schematic cross-sectional view of a wafer in a step for machining a contact hole on a Si wafer, and embedding a metal therein. There is a normal part 401 in which the metal and Si wafer are conducting, and a defective part 402 in which the metal and the Si wafer are not conducting due to a residual film from defective processing of the contact hole. In order to detect this defect, the wafer must be electrostatically charged, a voltage contrast image obtained by taking the potential difference produced by the electrical resistance difference of the normal part and defective part as a difference in the number of secondary electrons detected by a detector 411, and the voltage contrast difference between the normal part and defective part measured. In the voltage contrast image, the wafer surface may be given a (1) positive charge or (2) negative charge according to the structure and inspecting conditions of the wafer to be inspected. The contrast of the pattern varies with the potential of the wafer.

To detect a defective electrical property using the aforesaid voltage contrast, and to detect a defect with high sensitivity, the wafer surface must be suitably charged. To obtain results which are highly reliable and reproducible, the electrostatic charge on the wafer surface must always be constant. Therefore, a method to measure the electrostatic charge on the wafer surface precisely is required.

Here, the potential measurement method by a conventional electron beam tester will be described. The schematic view of a prior art potential measurement method using an energy filter is shown in FIG. 3A. In FIG. 3A, 92 is a deflector, 87 is a first grid, 88 is a second grid, 86 is a sample, and the sample 86 is irradiated by an electron beam 81. The electron beam 81 can irradiate arbitrary points on the sample 86 due to the deflector 92. A potential 82 of this sample 86 with respect to earth is unknown. It is attempted to measure this unknown potential 82 by secondary electrons. Secondary electron 93 emitted from the sample 86 are accelerated by the first grid 87 to which a potential 84 of +10 to +100 V is applied, and most pass through the first grid 87. A potential 83 (energy filter potential) of, for example, −5 V is applied to the second grid 88. Secondary electrons 95 which pass through the second grid 88 are detected by a secondary electron detector 89. If the potential 83 applied to the second grid 88 is changed, for example to −30 to +30 V and the corresponding output of the secondary electron detector 89 is recorded on a XY recording waveform 91, a curve like A of FIG. 3B will be obtained. In general, this is referred to as an S curve. FIG. 3B shows the analysis characteristics of the energy filter obtained by the aforesaid operation. The horizontal axis is the potential of the second grid 88, and the vertical axis is the secondary electron detector output. Curves A, B are curves obtained for two different sample potentials. In both curves, the secondary electron detector output decreases as the potential of the second grid 88 becomes more negative. The curve A is shifted to the left-hand side compared with the curve B. This shows that the sample potential of curve A is a more negative potential. For the actual potential measurement, the output of the secondary electron detector 89 is set to the value shown by for example the arrow C, and the intersection points $V_A$, $V_B$ with the S curve are obtained. This difference ($V_A$−$V_B$) becomes the variation amount of the sample potential 82. If the curve A is for the case of a sample potential of 0, ($V_A$−$V_B$) is the sample potential when B is measured (e.g., Scanning Electron Microscopy, Vol. 1, p. 375). To prevent the effect of fluctuation in the irradiation electric current of the primary electron beam, or the amount of secondary electron emission, there is also the method of differentiating the S curve shown in FIG. 3B by the second grid voltage, normalizing it, and calculating the variation amount of the sample potential 82 from the curve shift amount (e.g., JP 1986-239554 A).

SUMMARY OF THE INVENTION

The problem inherent in the prior art technique will be described using FIG. 3. Most of the secondary electrons emitted from the sample 86 are picked up the first grid 87 to which a positive electropositive potential was applied, the potential applied to the second grid 88 is changed, the S curve is obtained by recording the corresponding output of the secondary electron detector 89, and the potential of the sample is computed from the S curve. This technique is used to measure the potential of interconnections on the semiconductor device. The potential of the interconnections is a fixed potential under given operating conditions. Since the effect of irradiation by the primary electron beam can be disregarded, a more precise potential can thus be measured.

However, for most semiconductor devices which are targets for inspecting measurement using an electron beam, there is an insulating film on the surface. If the surface potential of the semiconductor device is measured by the described method, the following problem occurs:

(1) The electric charge of the surface regions of the insulating film is spatially re-distributed by irradiation with the primary electron beam, the surface potential changes, and the potential of the actual insulating film surface cannot be measured precisely.

The following secondary problems also occur:

(2) To enhance the resolution of the SEM image, the primary electron beam is first accelerated to several keV, and then decelerated to about several hundred −1 keV by applying a retarding voltage to the wafer holder. This method is widely applied to inspecting and measurement apparatus using charged particles. Due to this, the secondary signal emitted from the surface of the semiconductor device is also accelerated by the retarding potential to several keV. However, to measure the potential of the wafer surface by the aforesaid energy filter, the secondary signal must be decelerated to several eV, so a strong electrostatic lens effect may occur which decreases the resolution of the primary electron beam. To avoid such an adverse effect, more grids have to be used, the energy of the secondary signal must be reduced gradually and the S curve then measured. Since the construction of the energy filter becomes more complex, the transmissivity of the secondary signal decreases and operating condition restrictions occur.

(3) Due to potential distortion of the grid vicinity, the resolution of the energy filter will decrease.

Thus, not only must an energy filter of complex construction be used, but also, the surface potential of the wafer cannot be measured with high precision.

The present invention therefore aims to provide an inspection and measurement apparatus and inspection and measurement method which can measure the potential of a sample with higher precision than the prior art technique. It also aims to provide an inspection and measurement apparatus which can measure potential by means of an easy construction.

In order to attain the aforesaid object, when the inventors observed the S curve for semiconductor devices used as inspection and measurement targets, they discovered that the variation of the potential of the test sample surface could be suppressed by optimizing the energy of the irradiating primary electron beam. Here, optimization of the energy of the primary electron beam means that the irradiation energy (landing energy: $E_{Land}$) of the primary electron beam is suppressed so that the secondary particle yield is 1 or a value near 1. Here, the secondary particle yield, when the primary charged particle beam irradiates the sample, is the number of secondary particles generated per unit primary particles.

Therefore, the test sample is irradiated with the primary electron beam, two S curves, i.e., the dependency of secondary particle (e.g., secondary electron or reflected electron) signal strength on sample charge control voltage, are observed, and the surface potential of the test sample is calculated from the difference of the charge control voltage of the S curve equivalent to a predetermined secondary particle signal strength.

When the S curves are observed, if the control electrode is installed above the sample and facing the sample to be inspected, the S curves can be acquired without using an apparatus of complex construction such as an energy filter and plural grids. Hence, it is possible to measure the potential of the sample surface.

Here, for convenience, the potential of the sample was calculated from the result of measuring the S curve, but even if the S curve is not measured, the surface potential of the sample can still be measured. This is because, among the data which constitute the S curve, two points are theoretically sufficient to calculate the surface potential of the sample.

According to the invention, when measuring the surface potential of a semiconductor device, a more precise potential measurement than before, which is almost unaffected by the potential of the insulating film surface, can now be performed. Also, since the surface potential can be measured without equipment specialized for wafer surface potential measurement such as an energy filter, the manufacturing cost for the apparatus can be reduced.

Further, since the surface potential of the sample can be measured with high precision, in an apparatus wherein charge control of the sample surface must be performed to control the quality of an image which is to be acquired, quality control of the acquired image is easy. This advantage is particularly useful in an inspection/measurement apparatus using a scanning electron microscope such as a critical dimension measurement SEM or SEM inspection apparatus.

BRIEF DESCRIPTION OF THE DRAWINGS

FIG. 6 is a diagram describing one example of flow charts for the inspection according to the first embodiment of the;

FIG. 9 is a diagram describing the construction of a length measurement SEM apparatus according to a third embodiment of the;

FIG. 10 is a diagram describing an example of a length measurement flow chart according to the third embodiment of the; and FIG. 11 is a diagram describing the result of measuring the potential distribution on a wafer surface by the flow chart of FIG. 7 according to fourth and fifth embodiments of the.

DESCRIPTION OF THE PREFERRED EMBODIMENTS

Figure 1:
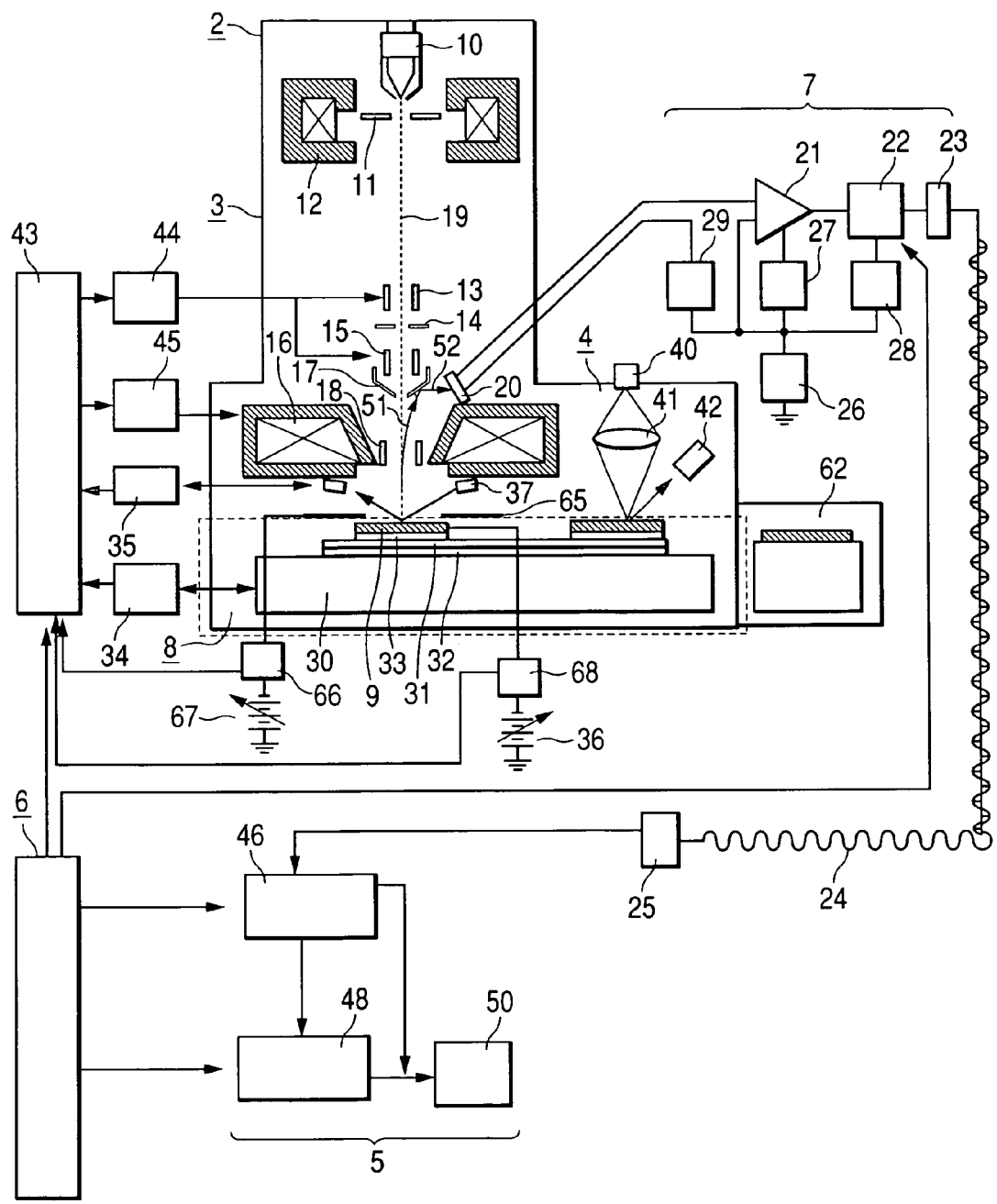
FIG. 1 is a diagram describing an SEM inspection apparatus according to a first embodiment.
Figure 2:
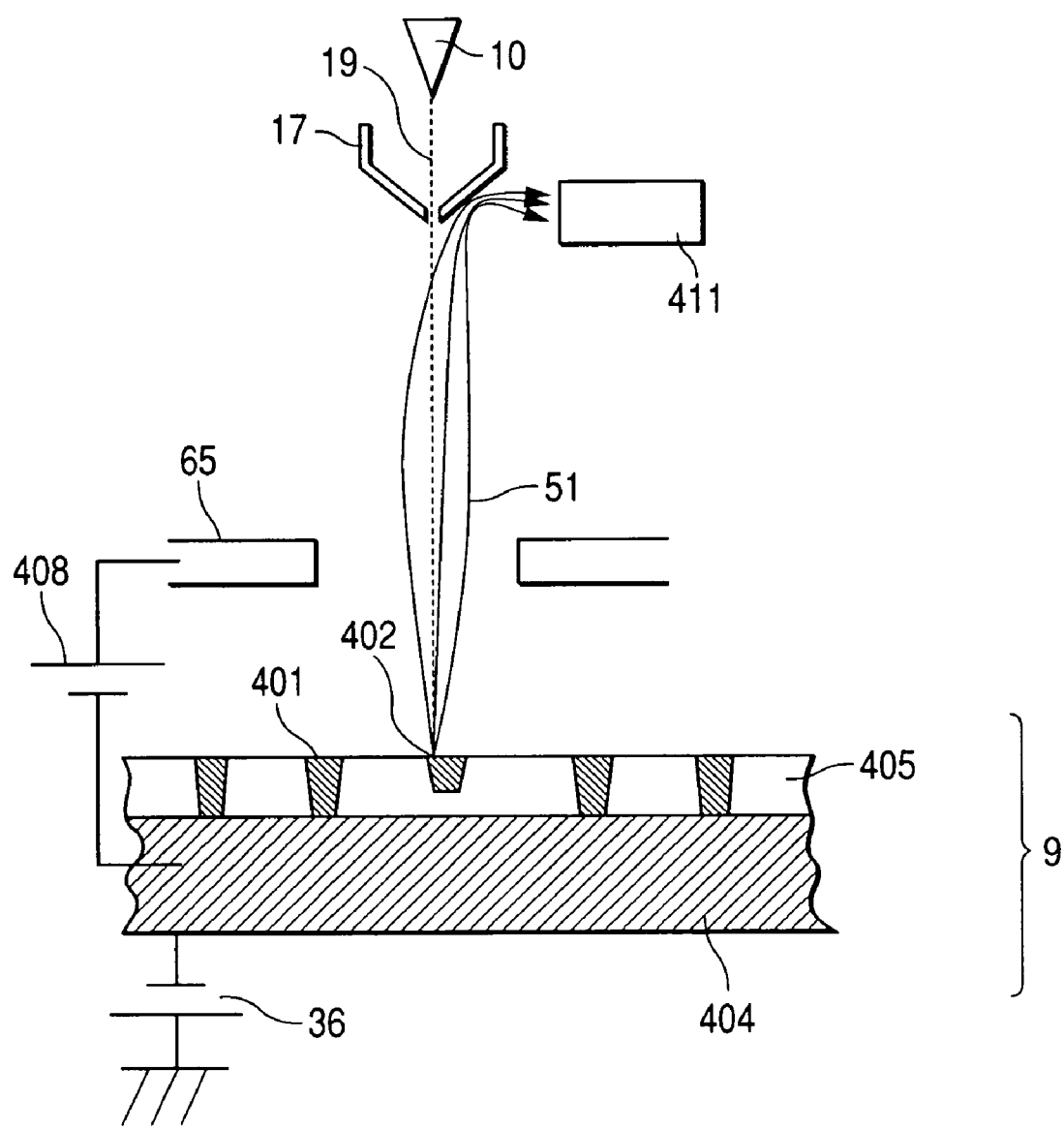
FIG. 2 is a diagram describing a voltage contrast image acquisition principle.
Figure 3A:
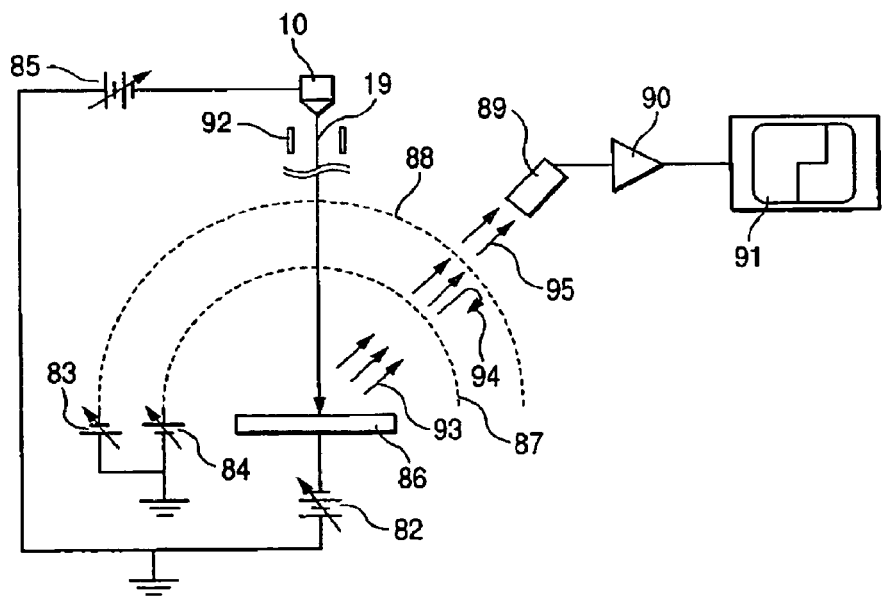
FIG. 3A is a diagram describing an EB tester construction and principle.
Figure 3B:
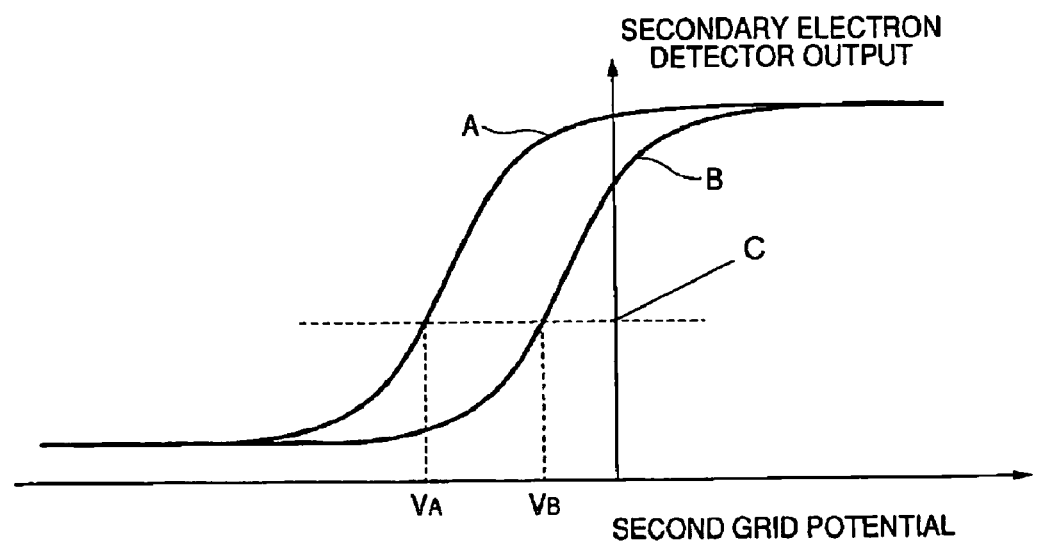
FIG. 3B is a diagram describing a principle whereby a sample potential is computed from an S curve.

Hereafter, referring to the drawings, an inspection method and apparatus according to one embodiment will be described in detail.

Embodiment 1

FIG. 1 shows the schematic view of the inspection apparatus relating to a first embodiment. The apparatus of this embodiment is a scanning electron microscope having a sample surface potential measurement means and charge control means, and may be applied to an inspection SEM, review SEM and measurement SEM. The scanning electron microscope shown in FIG. 1 is provided with a chamber 2 which is placed under vacuum, and a reserve chamber (in this embodiment, not shown) for transporting a wafer 9 as sample to the interior of the chamber 2. This reserve chamber is constructed so that it can be placed under vacuum independently from the chamber 2. In addition to the chamber 2 and the reserve chamber, the apparatus comprises a controller 6 and image processor 5. The interior of the chamber 2 broadly comprises an electron optics system 3, charge controller, detector 7, sample chamber 8 and optical microscope 4. In this embodiment, the chamber 2 means the whole vacuum vessel containing a sample chamber 8, and the electron optics system 3, charge controller, detector 7 and optical microscope 4 mentioned above operate inside the decompressed vacuum vessel. The sample chamber 8 is an enclosure wherein the sample stage is driven inside the chamber 2. The region enclosed by the dotted line of FIG. 1 corresponds to the sample chamber. The sample to be inspected may be a semiconductor wafer on which an interconnection pattern or circuit pattern is formed, a piece obtained by splitting off a part of a wafer, or a semiconductor chip on which a circuit is formed, but potential observations of samples other than semiconductor devices, such as a magnetic head, a recording medium or a liquid crystal panel can also be performed.

The electron optics system 3 comprises an electron source 10, electron beam drawout electrode 11, condenser lens 12, blanking deflector 13, scanning deflector 15, aperture 14, object lens 16, reflector plate 17, and ExB deflector 18. In the detector 7, a detector 20 is disposed above the object lens 16 in the chamber 2. The output signal of the detector 20 is amplified by a preamplifier 21 installed outside the chamber 2, and is converted to digital data by an A/D converter 22.

The charge controller comprises a charge control electrode 65, charge control electrode controller 66 and charge control power supply 67 which are installed facing the stage.

The detector 7 comprises the detector 20 in the chamber 2 which is placed under vacuum, preamplifier 21 outside the chamber 2, AD converter 22, optical transducer 23, optical fiber 24, electric transducer 25, high voltage power supply 26, preamplifier drive power supply 27, AD converter drive power supply 28, and reverse bias power supply 29. In the detector 7, the detector 20 is disposed above the object lens 16 in the chamber 2. The detector 20, preamplifier 21, AD converter 22, optical transducer 23, preamplifier drive power supply 27 and AD converter drive power supply 28 are floated at an electropositive potential by the high voltage power supply 26.

The sample chamber 8 comprises a sample stand 30, X stage 31, Y stage 32, wafer holder 33, position monitor length meter 34, and optical height gauge 35.

The optical microscope 4 is installed near the electron optics system 3 in the chamber 2 at a position sufficiently distant that they do not interfere with each other, and the distance between the electron optics system 3 and optical microscope 4 is known. The X stage 31 or Y stage 32 moves back and forth over the known distance between the electron optics system 3 and optical microscope 4. The optical microscope 4 comprises a light source 40, optical lens 41, and CCD camera 42.

Operating commands and operating conditions for each part of the apparatus are inputted and outputted from the controller 6. The controller 6 has a database in which control parameters and operating conditions of the electron optics system 3, X stage 31, Y stage 32 and other units are stored. Conditions such as the accelerating voltage when the electron beam is generated, electron beam deviation width, deviation rate, signal acquisition timing of detector and sample stand movement speed, are selected according to the purpose, and the parts of the apparatus are thereby controlled. The user may operate the apparatus by manual operation via a user interface, or may set the operating conditions beforehand by the controller 6 and operate the apparatus according to the setting. The controller 6 monitors position and height offsets from the signals of the position monitor length meter 34 and optical height gauge 35 using the correction control circuit 43, generates corrected signals from the result, and sends the corrected signals to the lens power supply 45 or scanning deflector 44 so that the electron beam always irradiates the sample in the right position.

In order to acquire an image of the wafer 9, this wafer 9 is irradiated with a finely focused beam 19, and secondary electrons, reflected electrons or both 51 are generated, the image of the surface of the wafer 9 being obtained by detecting these in synchronism with the scanning of the electron beam 19, and if required, the movement of the stages 31, 32.

The electron source 10 is a Schottky type electron source. By using this electron source 10 compared with, for example, a tungsten (W) filament electron source or conventional cold field emission type electron source of the prior art, a stable electron beam current can be ensured, so a voltage contrast image with little brightness variation can be obtained. The electron beam 19 is drawn from the electron source 10 by applying a voltage between the electron source 10 and drawout electrode 11. The electron beam 19 is accelerated by applying a high electronegative potential to the electron source 10.

Due to this, the electron beam 19 proceeds towards the sample stage 30 with an energy corresponding to this potential, is converged by the condensing lens 12, and is further focused by the objective lens 16 so as to irradiate the wafer 9 mounted on the X,Y stages 31, 32 on the sample platform 30. The scanning signal generator 44 which generates a scanning signal and blanking signal is connected to the blanking deflector 13, and the lens power supplies 45 are connected to the condenser lens 12 and objective lens 16. The arrangement is such that a negative voltage (retarding voltage) can be applied by the retarding power supply 36 to the wafer 9. Due to this, the primary electron beam is decelerated by adjusting the voltage of the retarding power supply 36, and the electron beam irradiation energy delivered to the wafer 9 can be adjusted to the optimum value without varying the potential of the electron source 10.

The secondary electrons or reflected electrons generated by irradiating the wafer 9 with the electron beam 19, or both 51, are accelerated by the negative voltage applied to the wafer 9. An ExB deflector 18 is disposed above the wafer 9, and the secondary electrons, reflected electrons or both which are thusly accelerated are deflected in a predetermined direction. The deflection amount can be adjusted by the voltage and magnetic field strength applied to the ExB deflector 18. Also, this electromagnetic field can be varied in synchronism with the negative voltage applied to the sample. The secondary electrons, reflected electrons or both 51 deflected by the ExB deflector 18 collide with a reflection plate 17 under predetermined conditions. When the accelerated secondary electrons, reflected electrons or both 51 collide with the reflection plate 17, second secondary electrons, reflected electrons or both 52 are emitted from the reflection plate 17.

The second secondary electrons and posterior scattered electrons 52 generated due to collision with the reflection plate 17 are led to the detector 20 by this sucking electrical field. The detector 20 detects the second secondary electrons, reflected electrons or both 52 generated when the secondary electrons, reflected electrons or both 51, which are generated when the electron beam 19 irradiates the wafer 9 and are accelerated to collide with the reflection plate 17, in synchronism with the scanning timing of the electron beam 19. The output signal of the detector 20 is amplified by the preamplifier 21 installed outside the chamber 2, and converted to digital data by the AD converter 22. The AD converter 22 immediately converts the analog signal detected by the detector 20 and amplified by the preamplifier 21 to a digital signal, and sends it to the image processor 5. The detected analog signal is digitized and transmitted immediately after detection, so a high speed signal with a high SN ratio can be obtained. Here, the detector 20 may be for example a semiconductor detector.

The wafer 9 is mounted on the X, Y stages 31, 32, and when scanning is performed, either the X, Y stages 31, 32 are held stationary while the electron beam 19 is scanned in 2 dimensions, or the X, Y stages 31, 32 are moved continuously at constant speed in the Y direction while the electron beam 19 is scanned in a straight line in the X direction. If a specific, relatively small region is to be scanned, the former method is used where the stages are held stationary for scanning, and if a relatively large region is to be scanned, it is effective to move the stages continuously at a constant speed for scanning. If the electron beam 19 must be blanked, control can be performed so that the electron beam 19 is deflected by the blanking deflector 13, and does not pass through the aperture 14.

In this embodiment, the position monitoring length measurement device 34 was a laser interference length measurement gauge. The positions of the X stage 31 and Y stage 32 can be monitored in real-time, and sent to the controller 6. Data such as the rotation speeds of the X stage 31, Y stage 32 and the motor of the wafer holder 33 are likewise sent to the controller 6 by the respective drivers. Based on this data, the controller 6 can precisely capture the region and position irradiated by the electron beam 19, and if required, the positional offset of the irradiation position of the electron beam 19 can be corrected by the correction control circuit 43 in real-time. Further, the region irradiated by the electron beam can be stored for each wafer.

The optical height measurement gauge 35 uses an optical measurement apparatus which is a measurement system different from that of the electron beam, for example a laser interference measuring device or a reflected light measuring device which measures the variation at a reflected light position, so the height of the wafer 9 mounted on the X, Y stages 31, 32 can be measured in real-time. In this embodiment, the wafer 9 is irradiated with white light from the light source 37, the position of the reflected light is detected by a position detecting monitor, and the height variation amount is computed from the positional variation. Based on the measurement data from this optical height measuring device 35, the focal length of the objective lens 16 which finely converges the electron beam 19 can be corrected dynamically, and the electron beam 19 can be irradiated so that it is always focused on a region to be inspected. Also, the warp and height distortion of the wafer 9 can be measured beforehand prior to electron beam irradiation, and the correction conditions for the objective lens 16 can be set for each inspection region based on the data obtained by the warp and height distortion measurement.

The image processor 5 comprises an image storage unit 46, computer 48 and monitor 50. The computer 48 has software for computing the potential of the sample surface based on the detection result of the detector 7, and software for defect inspecting of the sample by processing the detection result of the detector 7, and it performs potential detection computations together with defect inspecting computational processing. Also, although not shown in the diagram, the monitor 50 is provided with an information input means so that the user can input information required by the apparatus control system, the monitor 50 and information input means together forming the user interface of the apparatus. The image signal of the wafer 9 detected by the detector 20 is amplified by the preamplifier 21, and after digitization by the AD converter 22, converted to an optical signal by an optical converter 23, transmitted by an optical fiber 24, and after re-conversion to an electrical signal by an electrical converter 25, stored by the image storage unit 46.

The electron beam irradiation conditions for forming the image and the detection conditions of the detection system are set beforehand when the test conditions are set, filed and recorded in a database.

Figure 4A:
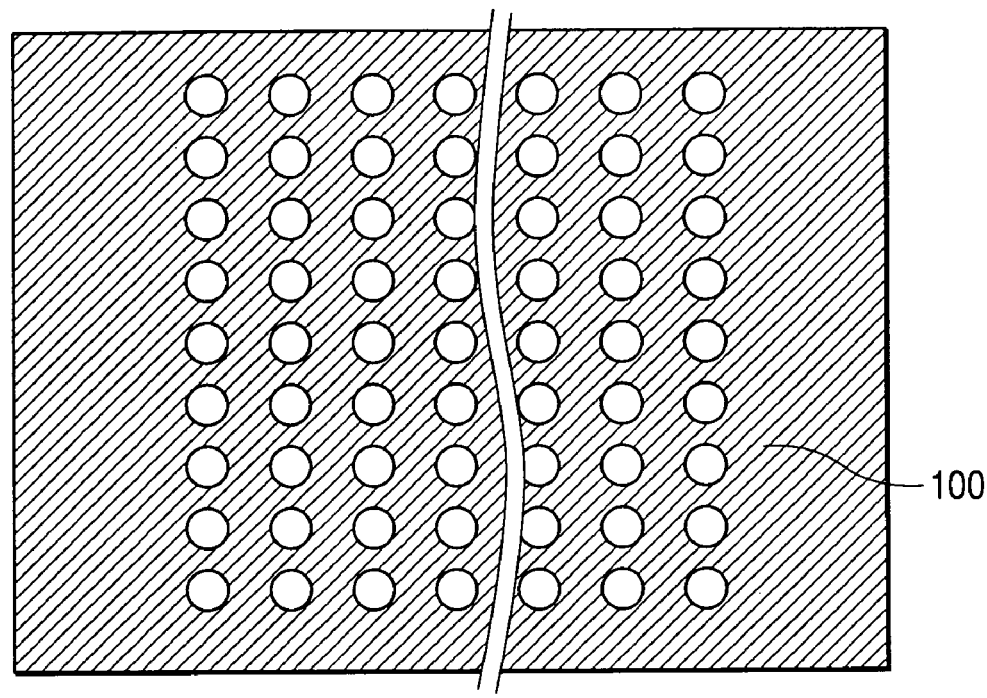
FIG. 4A is a diagram describing an SEM image of a semiconductor device.
Figure 4B:
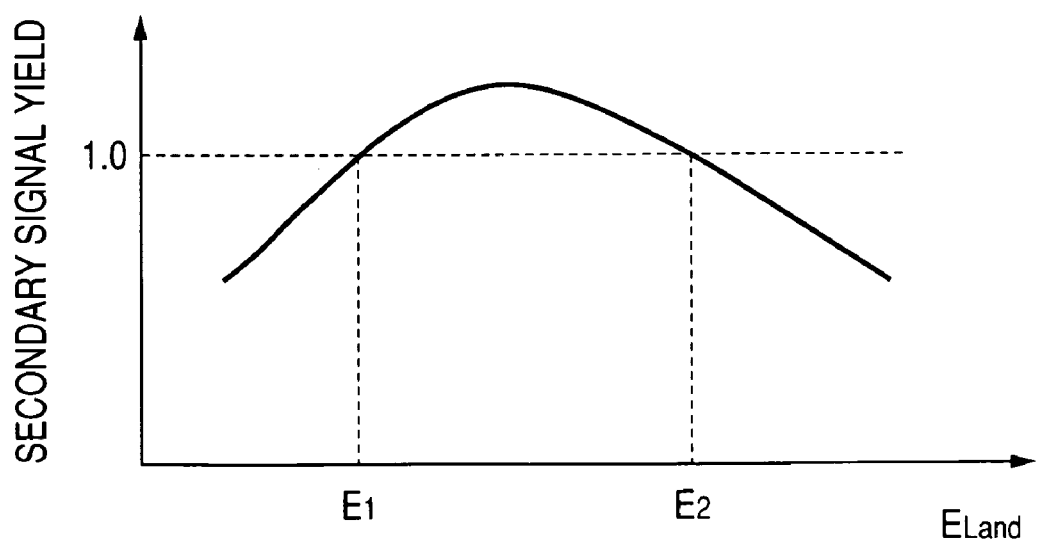
FIG. 4B is a diagram describing the result of measuring the variation of a secondary signal yield with an electron beam irradiation energy.

Next, FIG. 4A shows an example of the SEM image obtained by the apparatus of this embodiment. The SEM image of FIG. 4A is an SEM image of a semiconductor device obtained from the secondary signal amount emitted by a semiconductor device 100 detected by the detector when the surface of the semiconductor device 100 is scanned by a primary electron beam having a certain irradiation energy ($E_{Land}$). The white areas are holes, and the other shaded region is an inter-layer insulation film. The average value of the secondary signal from this shaded region or part thereof is calculated, and the yield of the secondary signal is computed. $E_{land}$ of the primary electron beam is varied by adjusting the voltage Vr applied to the wafer holder 33 (FIG. 1) by the controller 68, the yield of the secondary signal is computed by the same method, and the dependence of the secondary signal on $E_{land}$ of the primary electron beam is calculated (FIG. 4B). $E_{Land}$ ($E_2$) of the primary electron beam when the secondary signal is 1, is computed from the above dependence, and taken as $E_{land}$ of the primary electron beam used for potential measurement of the wafer surface.

Next, a region identical to that of the semiconductor device 100 is scanned by the primary electron beam having the aforesaid $E_{land}$, the potential of Vcc applied to the electrode 65 (FIG. 1) is varied from the more positive side (in FIG. 5, the value of Vcc is varied from right to left), the output of the secondary electron detector 20 (FIG. 1) corresponding to each Vcc value is recorded, and the S curve 41 (FIG. 5) is acquired. Since the yield or the secondary signal is 1 or close to 1, the emitted secondary signal does not return to the wafer surface until a push-back field is generated on the wafer surface, and the effect of the potential of the device surface due to the measurement can be ignored. By comparing with a reference S curve 40 obtained under identical measurement conditions, the surface potential of the semiconductor device to be measured is computed ($V_B - V_A$). Alternatively, computations such as differentiation and normalization are performed on the curves 40, 41 obtained by the measurement, and the aforesaid potential is computed from the peak shift amounts of the resulting curves 42, 43 ($V_D - V_C$).

As described above, in the apparatus according to this embodiment, the surface potential of a sample can be measured more precisely, and almost unaffected by the surface potential of the semiconductor device itself. However, due to variation in the Vcc condition during measurement, it may be affected by the potential of the insulation film. In this case, the image acquisition position may be changed for each image acquisition. Also, if required, the electrostatic charge may be mitigated by irradiating with an ultraviolet light beam or another electron beam.

Figure 6:
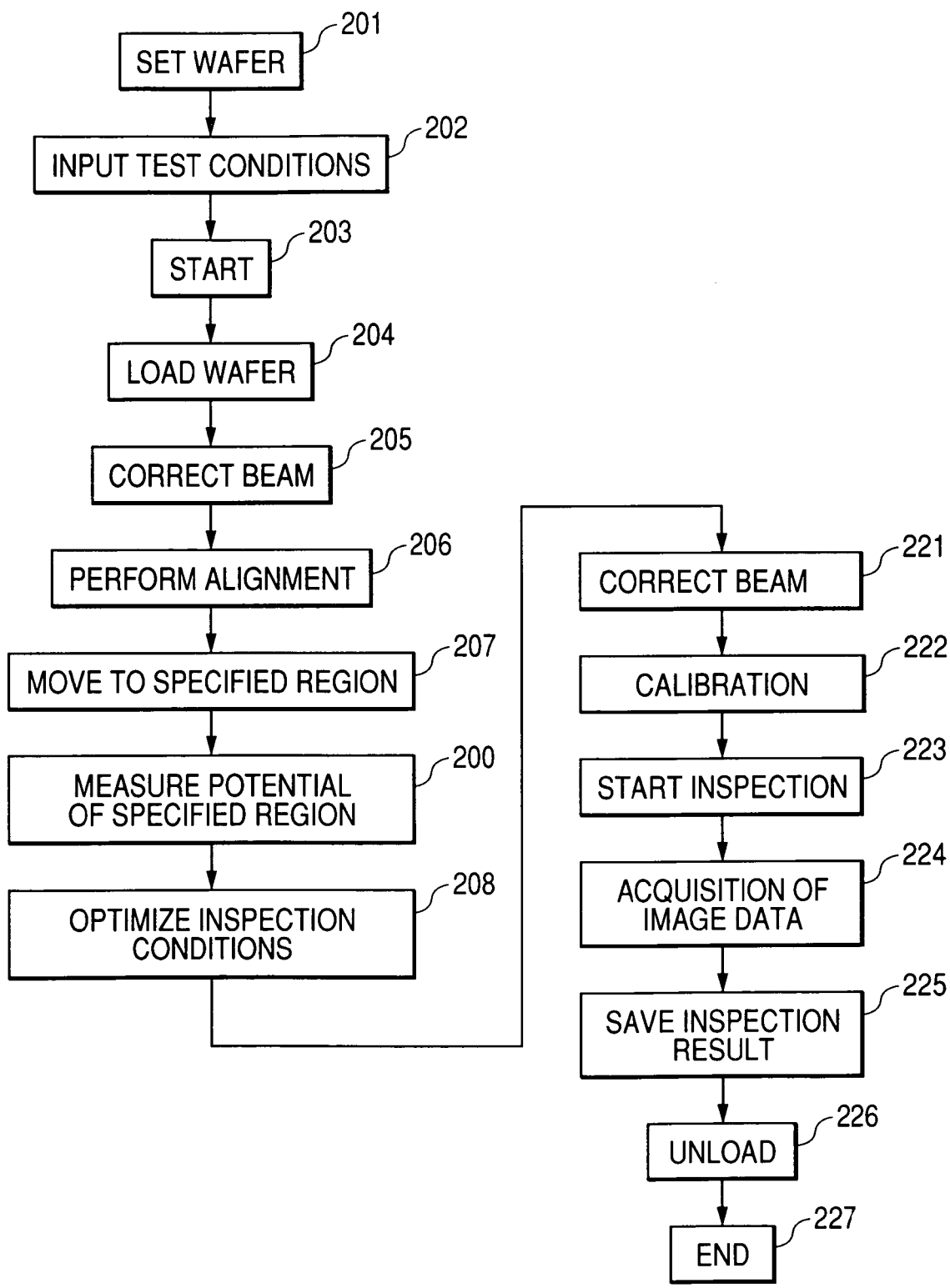

Next, the means for measuring the wafer surface potential using the apparatus shown in FIG. 1 will be described referring to the flow chart of FIG. 6.

First, in a step 201, a wafer cassette containing a wafer in any desired shelf, is positioned. The monitor displays an input request message to specify the wafer to be inspected, and the user specifies the shelf number of the cassette where the wafer is set by the information input means. Likewise, in a step 202, the monitor displays various input request messages to input inspection conditions, and the user inputs various inspection conditions via the information input means. The inspection conditions which are input include the electron beam current, electron beam irradiation energy, FOV (Field of View) of one screen, potential of the retarding power supply 36 and potential of the electrostatic control electrode 65. The individual parameters may be input, but normally a combination of these inspection parameters is entered into a database as an inspection condition file, inspection condition files being selected according to various ranges.

In a step 203 when Auto inspection is started, in a step 204, the set wafer 9 is loaded into the apparatus from the sample load/unload chamber 62. In the wafer transport system, even if the diameter of the wafer 9 is different, and even if the wafer shape is different such as orientation flat or notched, a holder for carrying the wafer 9 can be selected according to the wafer size and shape. This wafer 9 is transferred from the wafer cassette to the holder by a wafer loader comprising an arm and reserve vacuum chamber or the like, held fixed, placed under vacuum in the wafer loader together with the holder, and transferred to the chamber 2 which is already under vacuum in a vacuum pump system.

After the wafer is loaded, in a step 205, the electron beam irradiation conditions for each part of the apparatus are set by the controller 6 based on the input inspection conditions. The apparatus parts comprise for example a position monitor length gauge 34, optical height gauge 35, lens power supply 45 and scanning deflector 44, but also include all control parts required to control electron beam irradiation. The stage 32 is then moved so that the first beam correction pattern on the wafer holder is below the electron optical system, a voltage contrast image of the beam correction pattern is acquired, and focus/no-focus is adjusted by this voltage contrast image. This is then moved to a predetermined position on the wafer 9, an SEM image of the wafer 9 is acquired, and brightness and contrast are adjusted. Here, if it is required to vary the electron beam irradiation conditions, another beam correction may be performed. Also, the correlation between height information from the optical height gauge 35 and the focal point conditions of the electron beam can be calculated, and the focal point conditions adjusted automatically from the wafer height detection result without adjusting the focus each time the voltage contrast image is acquired thereafter.

In a step 206, to observe a first alignment coordinate by the optical microscope 4, the set wafer 9 is moved by the X, Y stages 31, 32. From the monitor 50, an optical microscope image of the alignment pattern formed on the wafer 9 is observed and compared with an identical pattern image stored beforehand, and a position-corrected value of the first coordinate is computed. Next, it is moved a fixed distance from the first coordinate to a second coordinate to where there is an equivalent circuit pattern to that of the first coordinate, an optical microscope image is observed in the same way, compared with a circuit pattern image stored for alignment, and the position correction value of the second coordinate and rotation offset amount relative to the first coordinate are computed.

Hence, when preparations such as predetermined corrections by the optical microscope 4 and test region settings are complete, the wafer 9 is moved underneath the electron optical system 3 by moving the X, Y stages 31, 32. When the wafer 9 is under the electron optical system 3, the same procedure as that of the alignment procedure performed by the optical microscope 4 is performed by the SEM image. The SEM image in this case is acquired by the following method. The electron beam 19 is scanned in two-dimensions in the XY direction by the scanning deflector 15 to irradiate the same circuit pattern as that observed by the optical microscope 4 based on the stored, corrected coordinate values in the positioning by the optical microscope image. Due to this two-dimensional scanning of the electron beam, the secondary electrons, reflected electrons or both 51 emitted from the observed site are detected by the construction and action of the various parts which perform detection of emitted electrons, and an SEM image is thereby acquired. Since simple inspection position confirmation, positioning and position adjustment have already been performed using the optical microscope image, and a rotation correction has already been made, the positioning, position correction and rotation correction can be performed with higher resolution, higher magnification and higher precision than with an optical image. When the electron beam 19 irradiates the wafer 9, the irradiation position is charged. To avoid the effect of this charge during inspecting, in pre-inspection preparations such as the aforesaid position rotation correction and inspection region setting, the circuit pattern irradiated by the electron beam 19 is pre-selected to be a circuit pattern outside the inspection region, or an equivalent circuit pattern of a chip or die outside the inspection region on the wafer is selected automatically by the controller 6. The alignment results obtained by this procedure are sent to each controller. During inspecting, rotation or position coordinates are corrected by the controllers.

Figure 7:
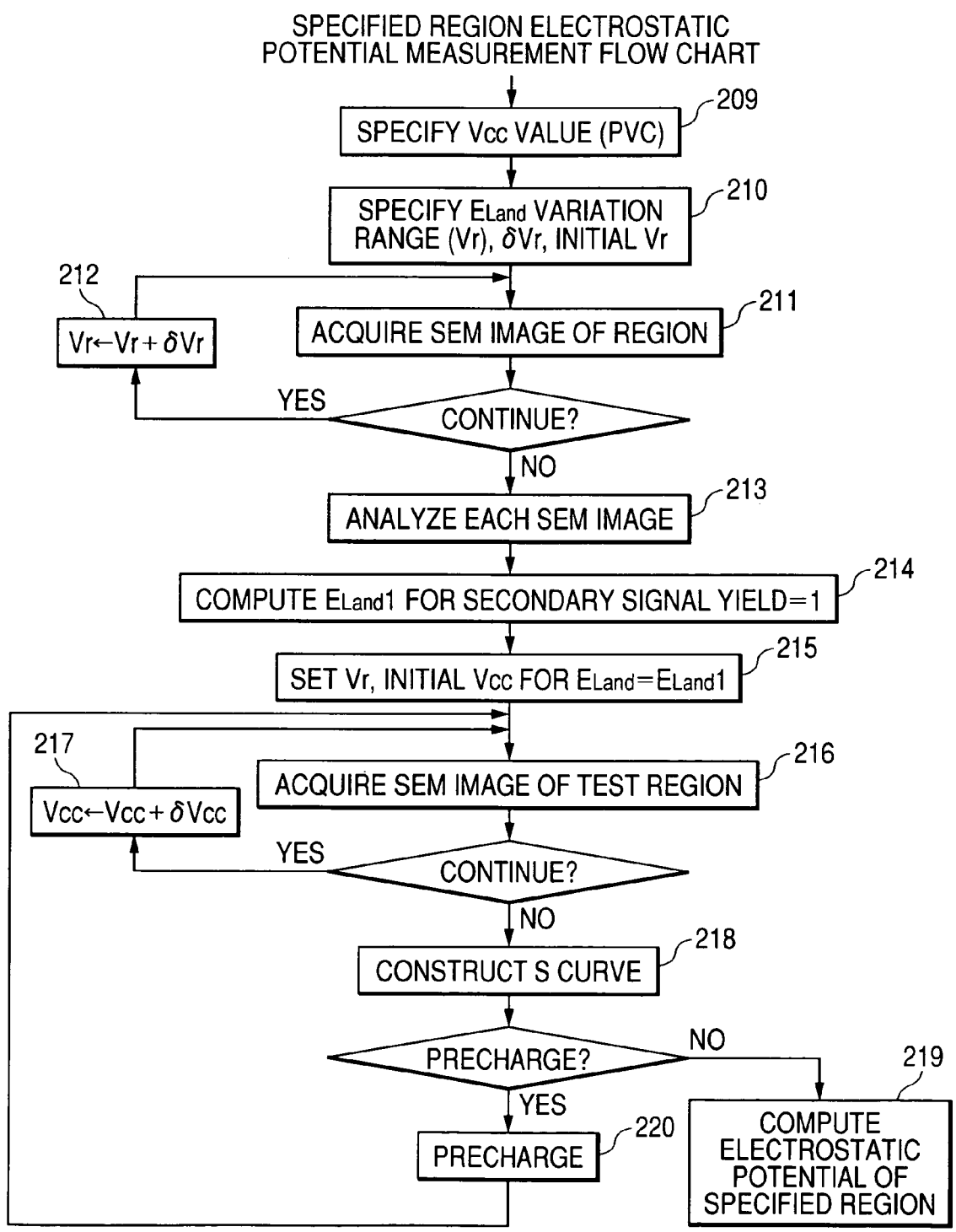
FIG. 7 is a detailed flow of the potential measurement portion in FIG. 6.

When the step 206 is complete, the X, Y stages are moved, and the specified region of the wafer is moved to the irradiation region of the primary electron beam (step 207). When the step 207 is complete, a step (step 200) for electrostatic charge potential measurement of the specified region is started. FIG. 7 shows the details of the process performed in the step 200. Hereafter, the flow chart 200 (steps 209-217) of the potential measurement of the specified region will be described. In the example describe in FIG. 7, the potential Vr of the holder 33 is varied under a probe current is restricted, however, the measurement under other measurement conditions could be taken into account in the same way. First, in the step 209, the request for setting the voltage Vcc is displayed on the monitor 50, and the user sets following values through via the information input means connected to the monitor 50; the voltage range (minimum value Vcc1, maximum value Vcc2), the increment width $\delta$Vcc of the voltage Vcc applied to the Vcc electrode. To detect the secondary electron signal emitted from the wafer without it returning to the wafer, an electric field is normally formed to pick up the secondary signal. In the step 210, the request for setting the retarding voltage Vr is displayed on the monitor 50, and the user inputs the minimum value Vr1, maximum value Vr2 and increment unit amplitude $\delta$Vr of Vr. In the step 211, when the initial condition Vr=Vr1 is met, scanning of the primary electron beam is performed and an SEM image is acquired. Subsequently, the Vr is progressively varied with the step size δVr until the Vr reaches to Vr2 (step 212), and the SEM image is acquired for each Vr condition. Here, when the image is acquired, auto brightness and contrast control of the signal value are not performed. In the step 213, the brightness and contrast of each image are analyzed, and in the step 214, Vr($E_{Land}$1) at which the secondary signal yield is 1 is computed by the computer 48. In the step 215, Vr computed by the computer 48 is sent to the retarding power supply controller via the controller 6. Also, the initial value (Vcc1 or Vcc2) of the voltage Vcc set by the user is sent to the charged state control electrode controller 66. These procedures permit setting of the retarding voltage and voltage applied to the control electrode 65. Subsequently, in the step 216, an SEM image is acquired, and brightness signal information acquired by the detector 20 is stored by the image processor 46. In the step 217, the voltage Vcc is varied with the increment unit δVcc, the voltage Vcc is reset while maintaining the voltage Vr constant, and an SEM image is acquired. This routine is repeated by the controller 6 until the voltage Vcc reaches its final value Vcc2. After SEM image acquisition is completed at Vcc2, the S curve is constructed in the step 218. Here, in constructing the S curve, the calculation is performed by computing the average value of signals outside the pattern shown in FIG. 4A. In the step 219, the processing that the obtained S curve is compared with the reference data, and then the potential of the specified region is calculated is executed by the computing unit in the computer 48. Also, in a case that adjustment of the potential of the wafer surface is needed before inspection, the charge/discharge procedure is performed by ultraviolet light or the electron source (step 220), an SEM image is again acquired, a new S curve is constructed (steps 216-218), and the variation of the wafer charge after processing is evaluated quantitatively by comparing with the data prior to charge/discharge (step 219). Here, the acquired S curve may also be differentiated and normalized in order to compute the potential of the specified region.

In the above description, the setting of Vr, Vcc in the steps 209, 210 was performed by the user inputting these values manually with viewing the monitor 50, while the setting values of Vcc1, Vcc2, δVcc, and Vr1, Vr2, δVr could be stored in a database equipped in the controller 6 in advance, consequently the flow chart of FIG. 7 is operated and controlled automatically by the controller 6. As for the operation of the flow chart of FIG. 7, the controller 6 does not necessarily have a database, and can still function if it is provided with storage means (i.e., a memory or storage) storing parameters for the control or conditions inputted by the user.

Figure 5A:
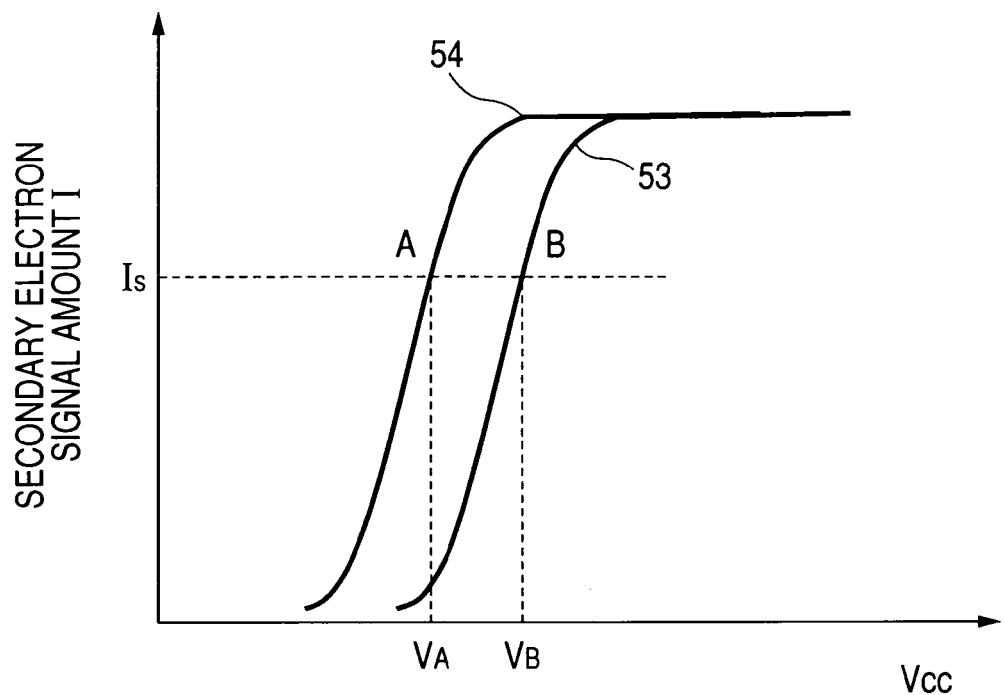
FIG. 5A is a diagram describing the computation of the potential of an inspection region by an S curve.
Figure 5B:
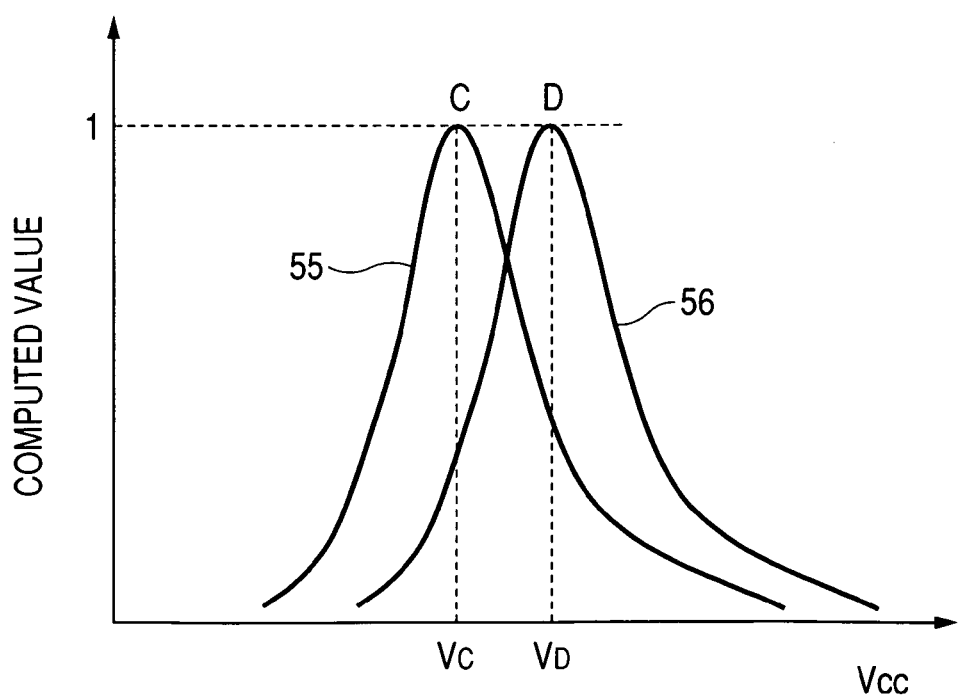
FIG. 5B is a diagram describing the computation of the potential of the inspection region by differentiating the S curve with respect to the Vcc potential and normalizing.

FIG. 5A shows the results of executing the steps in actual practice. FIG. 5A shows the results of measuring the S curves (respectively, curves 41, 40) before and after negative charging processing for the wafer surface of the semiconductor device, the shift amount (AB) of the both curves corresponds to the variation of potential of the wafer surface. Also, the results of differentiation and normalization of the curves 40, 41 are the curves 42, 43. The difference of the values Vcc of the positions C, D of the two peaks corresponds to the variation of potential in the measured region.

Next, in the step 208, inspection condition optimization is performed. Here, the contrast of the SEM images obtained at each Vcc in the aforesaid steps 215-217 are analyzed, and the Vcc value which gives the highest pattern contrast is taken as the inspection condition. If the irradiation energy of the primary electron beam used for the inspection is different from $E_{Land}$1, SEM images for each Vcc value are newly acquired and contrast-analyzed in the inspection region, the Vcc which gives the highest contrast being taken as the inspection condition.

Next, in a step 221, the beam correction of the step 205 is repeated. When the beam correction is complete, in a step 222, calibration is performed. The beam is moved to a second correction pattern mounted on the sample holder. The aim of the second correction pattern is to make the signal strength coincide with the signal from the voltage contrast image obtained in the inspection. The correction pattern may be contact holes of sufficiently low resistance ($10^3$ω or less), or a pattern in which contact holes of sufficiently high resistance ($10^{20}$ω or more) have been formed. Using the voltage contrast image of this pattern, the signal values of the sufficiently low resistance part and high resistance part are corrected. The sufficiently high resistance part may be an insulating part without a pattern. In view of this result, the beam is moved on the wafer 9, voltage contrast images of pattern positions on the wafer are acquired, and calibration is performed.

In a step 223, the inspection is started. In a step 224, SEM images of defects and the like are acquired, and in a step 225, these SEM images are stored. When the inspection is complete, in a step 226, the wafer is unloaded, and in a step 227, the routine is terminated.

In the above inspection method, the potential of the wafer can be managed quantitatively for each inspection, the problems of inspection reproducibility and decreased defect detection sensitivity of the prior art can be resolved, and a high reproducibility, high sensitivity inspection can be performed.

When the surface potential is measured, an image is acquired each time Vcc is changed, but there are some cases when the effect of charge or contamination under the above conditions cannot be ignored. In this case, to eliminate these effects, ultraviolet light irradiation may be performed. Alternatively, each time the inspection conditions are changed, the position where the image is acquired may be changed.

If there is any shading of the image, the flow chart 200 for potential measurement of the specified region may be performed after applying a shading correction.

Embodiment 2

If there are plural types of patterns in the wafer, the potential of each pattern will be different even if a precharge is performed on the whole wafer prior to the inspection. In this embodiment, a method will be described for determining the inspection conditions in this case.

Figure 8:
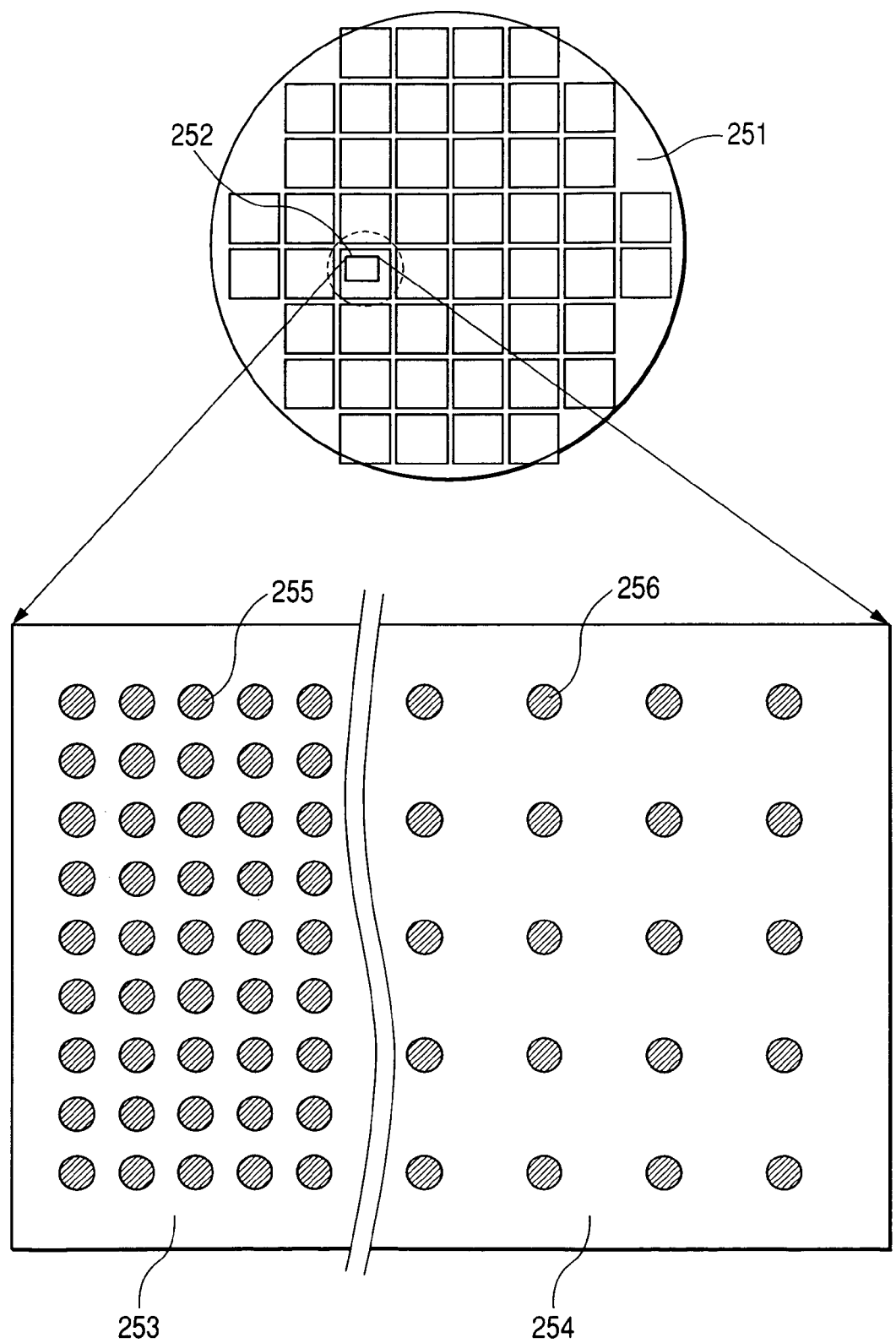
FIG. 8 is a diagram describing SEM images in which different pattern density portion is existing, according to a second embodiment.

In a die 252 of a wafer 251 of FIG. 8, patterns 255, 256 were made, respectively. From measurements by the method of the flow chart 200 for potential measurement of a specific region, the electrostatic potentials of the regions 253, 254 were −5 V and −10 V, respectively. In this case, (1) the average value of the optimum inspection conditions (e.g., Vcc value) estimated for both regions was used, or (2) the measurement was performed plural times varying the inspection conditions for each pattern, these methods being selected as required. Method (1) has an advantage that the inspection time is short as the whole surface is inspected under the same conditions, even though the inspection conditions deviate slightly from the optimum value so the sensitivity decreased to some extent. On the other hand, Method (2) has an advantage that inspection can be performed with a high sensitivity as the inspection conditions are optimized for the different patterns, however, inspection time becomes long as the inspection should be carried out on two occasions.

Embodiment 3

In this embodiment, an example will be described where a pattern dimensional measurement was performed using a length measuring SEM.

Figure 9:
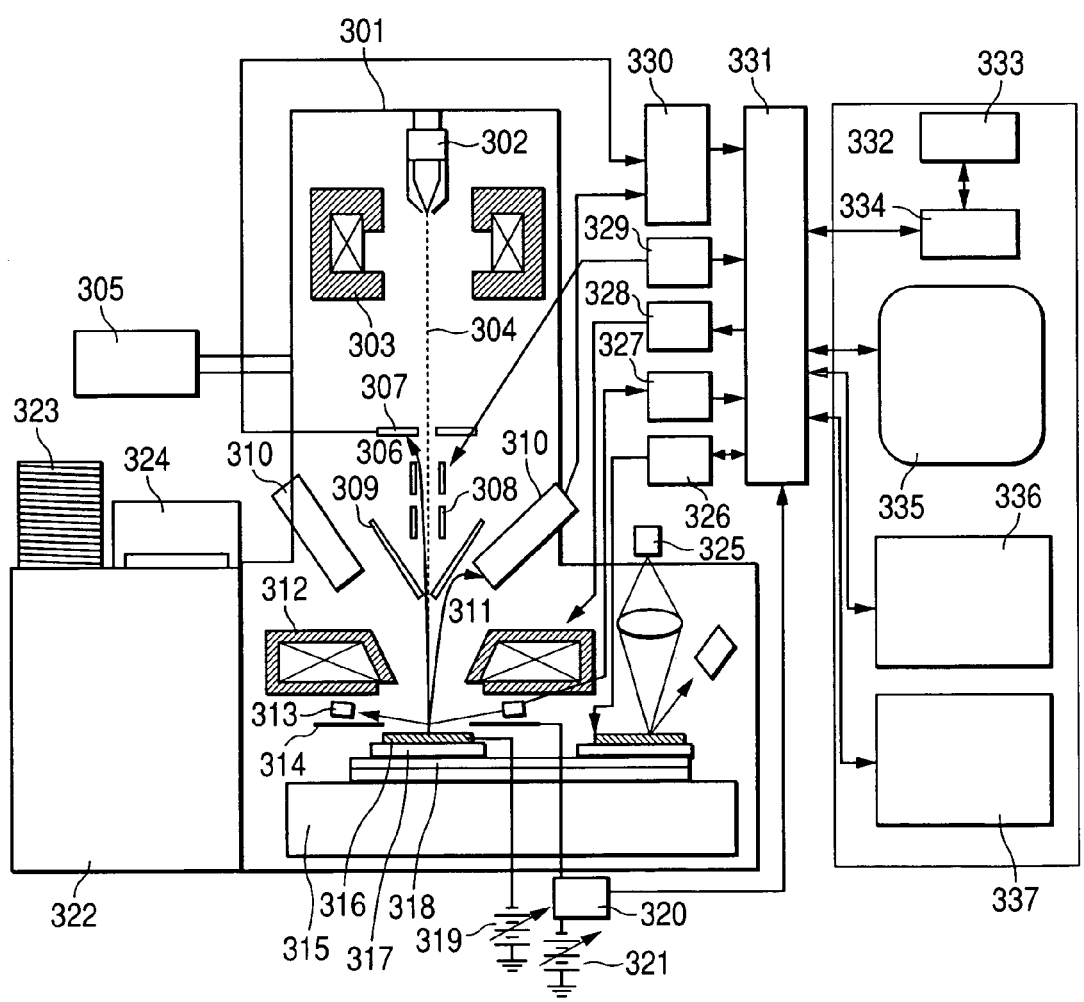

FIG. 9 shows an example of the construction of the length measurement SEM of this embodiment. The apparatus comprises an electron optical system 301, stage mechanism system 315, wafer transport system 322, vacuum discharge system 305, optical microscope 325, control system 331, control unit 332, and electrostatic controller.

The electron optical system 301 comprises an electron source 302, condenser lens 303, objective lens 312, first detector 310, second detector 307, deflector 308, reflecting plate 309, and wafer height detector 313. Reflected electrons 311 and secondary electrons 306 emitted by irradiating a wafer 316 with a primary electron beam 304 are detected by the first detector 310 and second detector 307, respectively.

The stage mechanism system 315 comprises an XY stage 318, holder 317 for mounting a wafer as a sample, and retarding power supply 319 for applying a negative voltage to the holder 317 and wafer 316. A laser length measurement position detector is attached to the XY stage 318.

The wafer transport system 322 comprises a cassette mounter 323 and wafer loader 324, the wafer holder 317 moving back and forth between the wafer loader 324 and XY stage 317 with the wafer 316 mounted thereupon.

The control system 331 comprises a signal detection system controller 330, beam deflection correction controller 329, electron optical system controller 328, wafer height sensor detection system 313, and a mechanism and stage controller 326. The control unit 332 comprises an operating screen and control panel 335, image processor 336, and image/measurement data storage unit 347.

The electrostatic charge controller comprises an electrode 314 installed facing the stage, charging control electrode controller 320, and charging control power supply 321.

Figure 10:
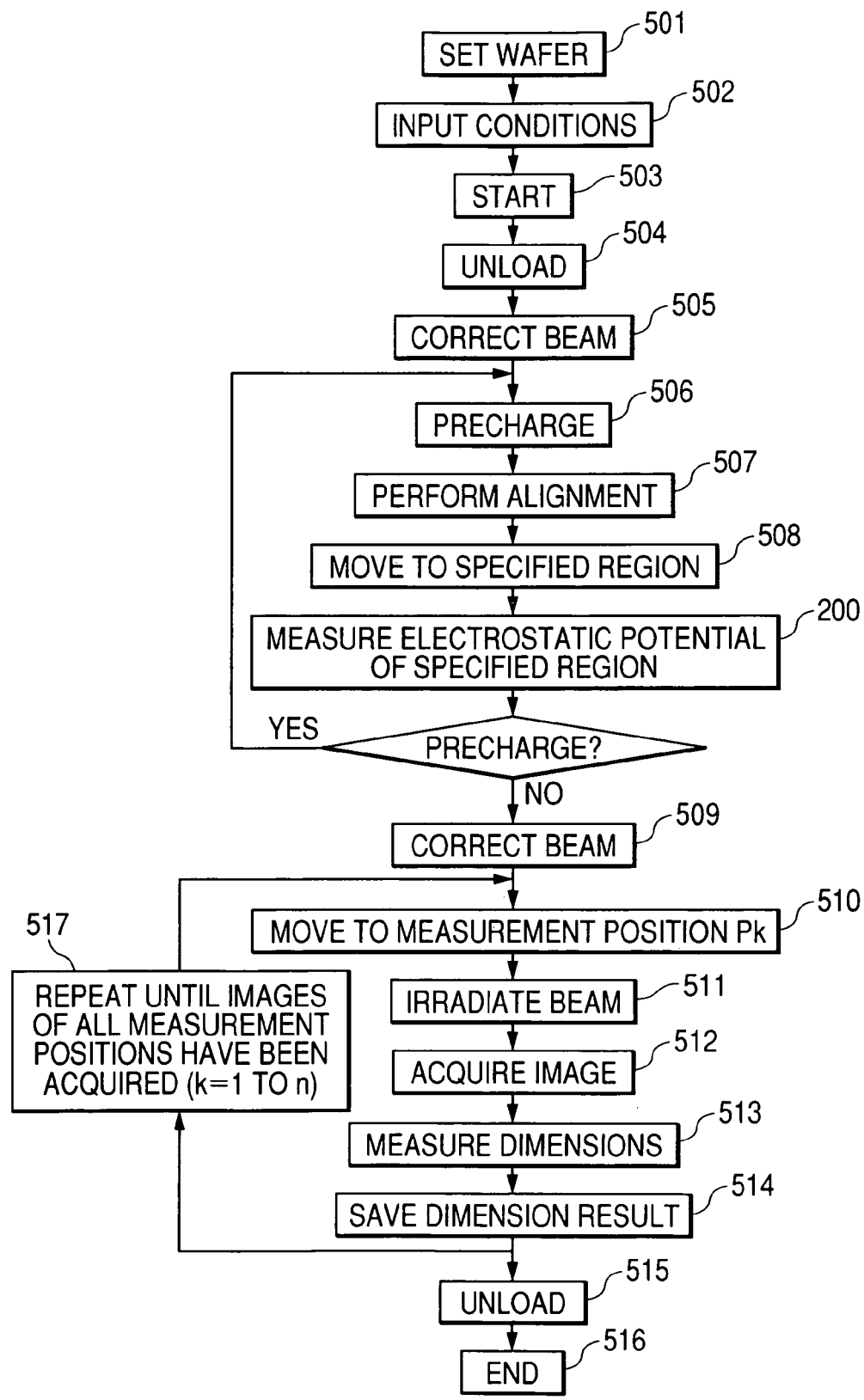

Next, the operation of each part of FIG. 9 will be described referring to the flow chart of FIG. 10.

First, in a step 501, the wafer cassette in which the wafer 316 is set at any desired position is placed in the cassette mounter 323 in the wafer transport system 322. Next, in a step 502, to specify the wafer 316 to be measured, the cassette shelf number on which the wafer 316 is set, is specified from the operation screen 335. Also, the measurement condition file name is input from the operation screen and control panel 335. This measurement condition file is built by combining various parameters for determining the measurement details. When input of the conditions required for measurement is complete, in a step 503, the automatic measurement sequence is started.

In a step 503, when the measurement is started, the set wafer 316 is first transported inside the length measurement apparatus. In the wafer transport system 322, even when the diameter of the wafer to be measured is different, or the wafer shape is different from the orientation flat shape or notched shape, the holder 317 on which the wafer 306 is mounted may be selected according to the wafer size and shape. The wafer to be measured is mounted from the cassette onto the holder 317 by the wafer loader 324 which includes an arm and reserve vacuum chamber, held fixed, and transported to the test chamber together with the holder.

In a step 504, the wafer 316 is loaded, and in a step 505, the electron beam irradiation conditions and focus/no-focus are adjusted based on the input measurement conditions. The electron beam irradiation conditions for each part are set from the electron optical system controller 328. In a step 506, precharge (charge/discharge) is performed using ultraviolet light or an electron source. In a step 507, alignment is performed using plural points on the wafer. The electron beam image at predetermined locations on the wafer 316 is acquired, and focus/no-focus is adjusted by the image. Also, the height of the wafer 316 is simultaneously calculated by the wafer height detector 313, the correlation between the height information and the electron beam focusing conditions is calculated, and from the wafer height detection results, the focusing conditions are automatically adjusted without having to focus on each occasion in subsequent electron beam image acquisitions. Next, the potential of the specified region is measured according to the flow chart 200, and precharge (charge/discharge) is repeated until the potential of the measurement region reaches the predetermined value. In a step 509, the rotation and coordinate values are corrected based on the alignment results, and the wafer is moved to the measurement position based on the various wafer information already read. High-speed, continuous electron beam image acquisition can then be performed.

In a step 510, after the wafer is moved to the measurement position, in a step 511 it is irradiated by the electron beam, and in a step 512, image data acquisition is performed. In the step 512, the acquired high magnification image is saved, if required, by the image/data storage unit 337. If required, plural types of image from plural detectors can be saved simultaneously depending on the setting. For example, the image from secondary electrons detected by the second detector 307 and the image from reflected electrons detected by the first detector 310, may be saved simultaneously.

In the step 512, when the image data is saved, pattern dimensional data is extracted from the image information by the image processor 336, and this result is saved automatically (step 514). If required, this result is displayed on the operation screen 335. When the aforesaid sequence of operations has been completed for all measurement positions specified for one wafer, in the step 514, the wafer measurement result file (classification results file) is saved automatically, and the measurement result file is output to a specified location. Subsequently, in a step 515, the wafer is unloaded, and in a step 516, measurement is terminated.

By using this method, pattern dimensions can be always be measured in a fixed charge state, and fine pattern dimensions can be measured at high speed with high precision.

In this embodiment, if there is any shading in the image, measurements may be performed after performing a shading correction.

When the surface potential is measured, the image is acquired each time the irradiation conditions are changed, but it may occur that the charge under previous conditions and the effect of contamination cannot be ignored. In this case, to eliminate these effects, ultraviolet light irradiation may be performed. Alternatively, the image acquisition position can be changed each time the irradiation conditions are changed.

Embodiment 4

The inspecting and measurement was accelerated by converting the inspection/measurement conditions to a database using data comprising potential measurements at each position on the wafer surface as shown in Embodiments 1-3.

Figure 11:
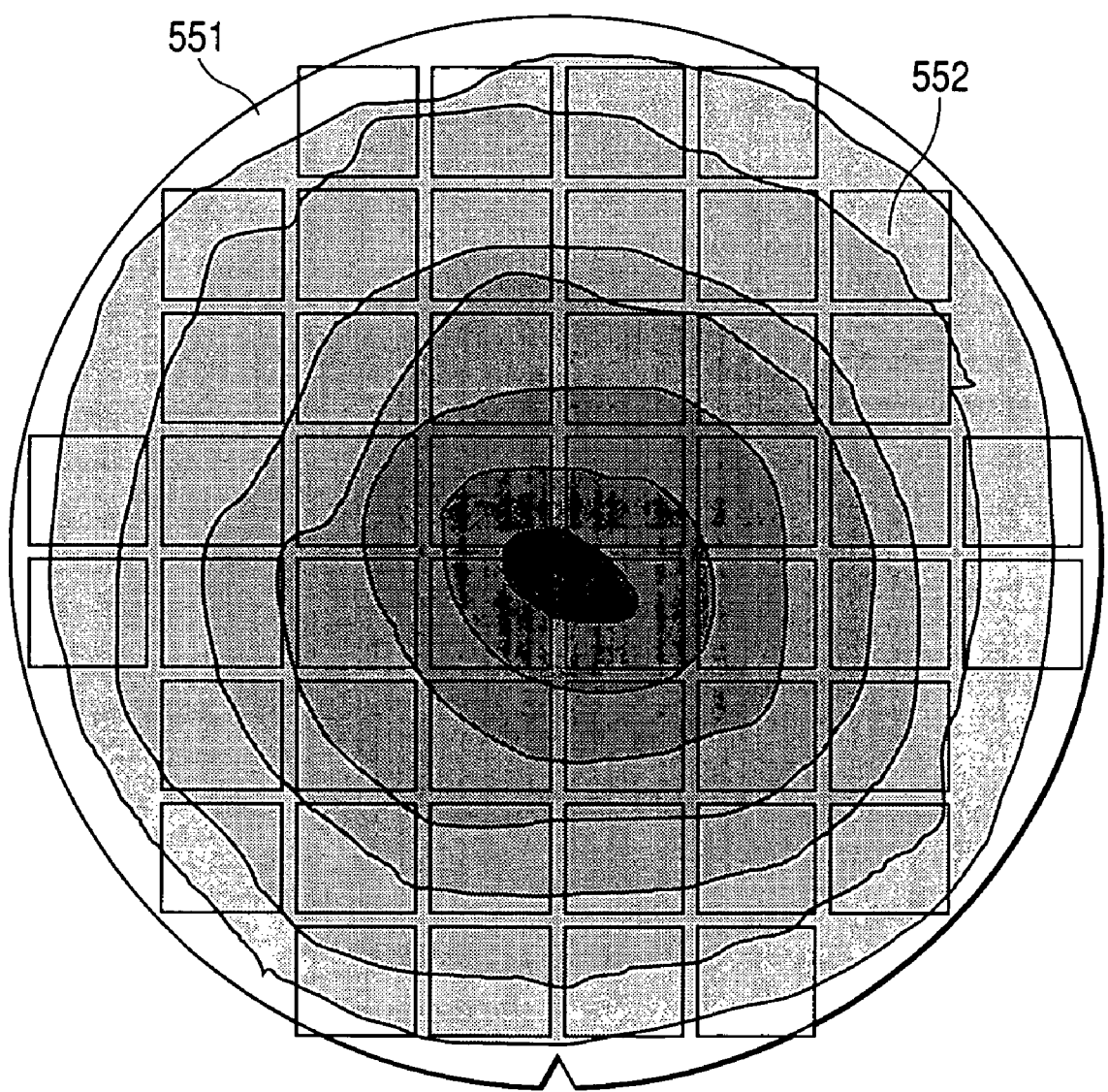

FIG. 11 shows the surface potential distribution of a wafer 551 measured by the flow chart 200. This distribution 552 may be obtained by measuring the surface potential by the flow chart 200 at several positions on the wafer surface, and predicting the potential distribution over the whole wafer surface from the obtained results. The potential measurement is carried out prior to performing inspecting and measurement, and the results are converted to a database, and stored in the data storage unit 337.

Next, inspecting and measurement of the wafer is performed using this database. An SEM image is acquired by reading the potential at each inspecting and measurement position into the correction control circuit 43 or control system 331 from the distribution 552, and adjusting the excitation current so that the secondary electron beam is focused at the inspecting and measurement position. Defect detection and dimensional measurement are performed from the obtained SEM image.

By using this method, inspecting and measurement can be performed so that the primary electron beam is always focused on the wafer surface, and high sensitivity defect detection, as well as high speed, high precision, fine pattern dimensional measurement, can thus be achieved.

The aforesaid embodiment can be applied to any inspecting and measurement device which uses a convergent charged particle beam such as an inspection SEM, review SEM and CD-SEM.

Embodiment 5

The inspecting and measurement was accelerated by converting the inspection/measurement conditions to a database using data comprising potential measurements at each position on the wafer surface as shown in Embodiments 1-3.

FIG. 11 shows the surface potential distribution of the wafer 551 measured by the flow chart 200. This distribution 552 may be obtained by measuring the surface potential by the flow chart 200 at several positions on the wafer surface, and predicting potential distribution over the whole wafer surface from the obtained results. The potential measurement is carried out prior to performing inspecting and measurement, and the results are converted to a database, and stored in the data storage unit 337.

Next, inspecting and measurement of the wafer is performed using this database. If the potential difference at each point in the wafer surface is relatively small, an SEM image is acquired by reading the potential at each inspecting and measurement position into the correction control circuit 43 or control system 331 from the distribution 552, and adjusting the retarding voltage 36 or 319 so that the primary electron beam is focused at the inspecting and measurement position. Defect detection and dimensional measurement are performed from the obtained SEM image.

By using the aforesaid method, inspecting and measurement can be performed with the primary electron beam always focused on the wafer surface simply by adjusting the retarding voltage. Compared to the case where the excitation current of a magnetic field objective lens is adjusted to focus the primary electron beam, the response speed is relatively fast and feedback to the focus can be performed in real-time, so inspecting and measurement can be performed more rapidly.

The aforesaid embodiment can also be applied to any inspecting and measurement device which uses a convergent charged particle beam such as an inspection SEM, review SEM and CD-SEM.

As described above, defect detection can always be performed at the required potential in a wafer which has been partially completed with a semiconductor device having a circuit pattern, therefore defect detection sensitivity and reproducibility can be greatly enhanced. Further, in a measuring device such as a length measurement SEM, by measuring the potential distribution on the wafer surface by global charge or the like, and feeding back this data to the control system of the optical system, automatic measurement can be performed more rapidly with higher precision, and productivity in semiconductor manufactured goods can be monitored with higher sensitivity and higher precision.

What is claimed is:

1. An inspection and measurement method which inspects an inspection sample by irradiating a primary electron beam to said inspection sample, and detecting either generated secondary electrons, reflected electrons, or both, comprising the steps of:
    measuring a potential of said inspection sample; and
    controlling the potential of said inspection sample based on information about this measured potential, wherein said potential measurement step comprises:
    retrieving a secondary electron beam intensity or reflected electron beam intensity for a standard sample;
    irradiating said inspection sample with a primary electron beam while energy is adjusted so that a secondary electron yield or reflected electron yield is 1 or approximately 1;
    measuring a secondary electron intensity or reflected electron intensity generated from said inspection sample by irradiation of said primary electron beam; and
    determining the potential of said inspection sample by obtaining a voltage difference between said measured secondary electron beam intensity or reflected electron beam intensity and the secondary electron beam intensity or reflected electron beam intensity for the standard sample.

2. A sample inspection method which inspects an inspection sample by irradiating said inspection sample with a primary electron beam and detecting generated secondary electrons, reflected electrons, or both, the method comprising the steps of:
    measuring the potential of said inspection sample, and controlling the potential of said inspection sample based on information about the measured potential, wherein said potential measurement step further includes the steps of:
    retrieving a first S curve corresponding to a secondary electron intensity or reflected electron intensity of a standard sample;
    irradiating said inspection sample with a primary electron beam adjusted so that the secondary electron yield or reflected electron yield is 1 or approximately 1, and acquiring a second S curve corresponding to a secondary electron intensity or reflected electron intensity of said inspection sample; and
    determining the potential of said inspection sample from the difference between the first S curve and second S curve taken at the same value.

3. The sample inspection method according to claim 1, wherein:
    the dependency of said secondary electron yield or reflected electron yield on the irradiation energy of the primary electron beam for said inspecting sample is measured, and the irradiation energy of said primary electron beam is adjusted.

4. The sample inspection method according to claim 3, wherein,
    when the dependency of the primary electron beam of said secondary electron yield or reflected electron yield on the irradiation energy is measured:
    the secondary signal or reflected electron yield irradiates a known standard sample and an inspection target region of said inspection sample by said primary electron beam; and
    the secondary electron yield or reflected electron yield of the inspection target region is estimated from the secondary signal or reflected electron intensity of the standard sample and the secondary signal or reflected electron signal of the inspection target region.

5. The sample inspection method according to claim 1, wherein the inspection sample is a semiconductor device on which a circuit pattern is formed; and when the irradiation energy of the primary electron beam for a secondary electron yield or reflected electron yield of 1 is computed, a step is performed to extract a signal from outside the region in which said circuit pattern was formed among the detected secondary electron image or reflected electron image, and calculate the irradiation energy of the corresponding primary electron beam when said yield is 1 by comparison with a signal extracted from an image of a position where said circuit pattern is not present.

6. The sample inspection method according to claim 2, wherein said secondary electron beam intensity or reflected electron beam intensity is measured by an electrode disposed near the inspection sample, and further comprising the steps of:

when measuring the surface potential of said inspection sample, detecting the secondary electron beam intensity or reflected electron beam intensity from a standard sample whenever the potential of said electrode changes and storing the variation of a secondary signal strength with electrode potential as reference data by storage means taking a conductor for which the potential is already known as the standard sample; and computing the potential of said inspection sample by comparing the secondary electron beam intensity or reflected electron beam intensity detected from the inspection sample with said stored reference data.

7. The sample inspection method according to claim 6, wherein, when computing the potential of said inspection sample, the potential of the inspection sample is computed by differentiating said secondary signal amount with respect to the potential of said electrode, and comparing the obtained results.

8. The sample inspection method according to any one of claims 1, 2, 3, 4, 5, 6 and 7 wherein:

suitable conditions for inspection and measurement are selected from an existing inspection and measurement condition database, and used as inspection conditions.

9. The sample inspection method according to any of claims 1 to 7, wherein said inspection sample with controlled potential is irradiated by the primary electron beam, a secondary electron beam image or reflected electron beam image is acquired, and a defect which exists in said inspection sample is detected by analyzing the acquired image information.

10. The sample inspection method according to any of claims 1 to 7, wherein:

a secondary electron beam image or reflected electron beam image of a first region and second region is acquired by irradiating the inspection sample with controlled potential by the primary electron beam; and a defect in said inspection sample is detected by comparing the obtained images of the first region and second region.

11. The sample inspection method according to any of claims 1 to 7, further comprising a step of acquiring an image in coordinates based on defect coordinates obtained from a visual inspection apparatus, and classifying the image based on shape, contrast, and imperfection information.

12. A sample inspection apparatus which analyzes a secondary electron image or a reflected electron image obtained by irradiating an inspection sample using a primary electron beam, comprising:

means for measuring a potential of said inspection sample, means for controlling the potential of said inspection sample based on the measured potential, and a computing unit to determine the potential of said inspection sample by comparing the secondary electron beam intensity or reflected electron beam intensity of said inspection sample with the secondary electron beam intensity or reflected electron beam intensity of a standard sample, wherein said potential measurement means comprises means for measuring a secondary electron or reflected electron intensity generated from said inspection sample by irradiating said sample with a primary electron beam with energy adjusted so that a secondary electron yield or reflected electron yield is 1 or approximately 1.

13. The sample inspection apparatus according to claim 12, wherein said potential measurement means comprises a control electrode provided above said inspection sample.

14. The sample inspection apparatus according to claim 12 or 13, further comprising:

a comparison computing unit for comparing said secondary electron image or reflected electron image with another image having the same pattern; and a computing unit for distinguishing a defective part on the circuit pattern of said inspection sample from results of said comparison computing unit.

15. The sample inspection apparatus according to claim 12 or 13, further comprising:

a computing unit which classifies said secondary electron image or reflected electron image for each type of defect.

16. The sample inspection apparatus according to claim 12 or 13, further comprising:

an electron optics system which irradiates an inspection sample with a primary electron beam; and control means for controlling said electron optics system,:

wherein said control means varies a focus of said primary electron beam based on the potential distribution of the inspection sample.

17. The sample inspection apparatus according to claim 13, further comprising:

a monitor which displays a request to specify the potential setting of said control electrode, and a request to set a region in which a surface potential of said inspection sample is measured, and information input means for responding to said requests.

18. A sample inspection method which inspects an inspection sample by irradiating said inspection sample with a primary electron beam and detecting generated secondary electrons, reflected electrons, or both, the method comprising the steps of:

measuring the potential of said inspection sample, and controlling the potential of said inspection sample based on information about the measured potential, wherein said potential measurement step further includes the steps of:

retrieving a first S curve corresponding to a secondary electron intensity or reflected electron intensity of a standard sample;

irradiating said inspection sample with a primary electron beam adjusted so that the secondary electron yield or reflected electron yield is 1, and acquiring a second S curve corresponding to a secondary electron intensity or reflected electron intensity of said inspection sample; and determining the potential of said inspection sample from the difference between the first S curve and second S curve taken at the same value.

* * * * *